United States Patent [19]

Yamashita et al.

[11] 4,340,811
[45] Jul. 20, 1982

[54] FOCUSING METHOD AND APPARATUS FOR USE IN AN OPTICAL SYSTEM

[75] Inventors: Nobuo Yamashita; Ken-ichi Nakahashi, both of Hachioji, Japan

[73] Assignee: Olympus Optical Co., Ltd., Japan

[21] Appl. No.: 126,661

[22] Filed: Mar. 3, 1980

[30] Foreign Application Priority Data

Jun. 12, 1979 [JP] Japan .................................. 54/73840

[51] Int. Cl.³ .............................................. G01J 1/20
[52] U.S. Cl. .................................... 250/201; 250/227
[58] Field of Search ............... 250/201, 204, 209, 227; 354/25; 350/96.26; 356/4, 5

[56] References Cited

U.S. PATENT DOCUMENTS

| | | | |
|---|---|---|---|
| 3,783,270 | 1/1974 | Kamachi | 250/201 |
| 4,153,834 | 5/1979 | Hayamizu | 250/227 |
| 4,163,148 | 7/1979 | Fritsche et al. | 350/96.26 |
| 4,257,705 | 3/1981 | Hosoe et al. | 354/25 |

*Primary Examiner*—David C. Nelms
*Attorney, Agent, or Firm*—Ostrolenk, Faber, Gerb & Soffen

[57] ABSTRACT

A focusing method for use in an optical system and a focusing apparatus used therefor employ an illumination unit. The method comprises effecting photometry of light reflected from an object which is to be observed and which is illuminated only by light from the illumination unit, and causing a movement of the optical system to focus it, the magnitude of the movement being determined by the amount of light measured by the photometric operation.

17 Claims, 4 Drawing Figures

FOCUSING METHOD AND APPARATUS FOR USE IN AN OPTICAL SYSTEM

BACKGROUND OF THE INVENTION

The invention relates to a focusing method and apparatus therefor which is used in an optical system, and more particularly, to a focusing method and a focusing apparatus which is used in an optical system such as an endoscope which is provided with an illumination unit to permit observation of an object which is illuminated by the light from the illumination unit alone or principally illuminated by such light even though extraneous light may be present which is relatively weak.

When observing and taking a picture of an object with an endoscope, a photographic camera or a microscope, such instrument must be focused onto the object to be observed or photographed. In the prior art practice, a focusing operation takes place by moving an objective lens or the like of an optical system until a point is reached where the most clearly defined image of the object is obtained, while observing it through the system.

More recently, a double image coincidence scheme or ultrasonic focusing scheme has been proposed for the purpose of achieving an automatic focusing operation, and is it beginning to be implemented for practical use. However, such focussing schemes proposed are complex in the arrangement of apparatus required therefor, and therefore are not suitable for use in an application such as an endoscope for which an object must be observed or photographed through a narrow tube or a bundle of optical fibers.

As is well recognized, endoscopes can be categorized into a flexible type and a hard type. In addition, they are classified into medical and industrial endoscopes depending on the intended applications. In any event, each of these types of endoscopes is provided with an illumination unit to permit observation or the taking of a picture of the interior such as a coeliac cavity of a living body or the interior of a machine arrangement which has no access for external light. An object located in such internal space must be illuminated with light from the illumination unit alone.

When using an endoscope of the hard type, an objective lens contained therein may be moved while observing an object with the naked eye until a clearly defined image of the object is obtained. In such instance, an observation optical system comprises a plurality of lenses which transmit or relay an image of the object. This results in the difficulty that even when the object is not in focus, the controlling action of the eyes of the human observer permits the image to be viewed sharply, rendering it difficult to accomplish a precise focusing.

With an endoscope of the flexible type, its observation optical system includes a bundle of optical fibers in order to permit observation of a narrow and tortuous coeliac cavity such as the stomach or the bronchus of a man or a complicated interior such as an aircraft engine. A part of the bundle which defines a flexible tube adapted to be inserted into the coeliac cavity or into the interior of the machine has a reduced thickness and an increased length, so that the described focusing schemes cannot be readily applied to such applications.

SUMMARY OF THE INVENTION

It is an object of the invention to eliminate the described disadvantages of the prior art by providing a focusing method for use in an optical system and an apparatus therefor which is capable of allowing a focusing operation in response to a photometric value of light reflected from an object being observed or photographed which is illuminated only by light from an illumination unit associated with an endoscope or the like.

According to the invention, the photometric value of light reflected from an object being observed or photographed is determined, and such value is utilized to evaluate the distance to the object being observed or photographed for focusing purposes. In this manner, a focusing operation can be achieved in a very simple manner and accurately, and the method of the invention is easily applicable to an optical system such as an endoscope which includes an elongated portion adapted to be inserted into the coeliac cavity or the interior of a machine and which is formed by a bundle of optical fibers or an assembly of relay lenses so that an object can be observed through the distal end thereof.

When the invention is applied to an increased depth within the field of object, as occurs when it is applied to an endoscope, a practically satisfactory focusing can be achieved with a few steps of adjustment, affording great convenience.

Where the invention is applied to an endoscope the hard type, focusing can be achieved in contradistinction to a conventional unsatisfactory technique in which focusing takes place while observing an image of the object.

DESCRIPTION OF THE PREFERRED EMBODIMENTS

In general, with an endoscope which is used to observe a coeliac cavity or the interior of a machine, no or little external light is available for the illumination of the interior. For this reason, it is provided with an illumination unit, supplying illuminating light to the object being observed.

When an object is illuminated by light from such illumination unit for the purpose of observation or for taking a picture thereof, it is known that the brightness of the object is inversely proportional to the square of the distance between the illumination unit and the object, and is proportional to the reflectivity of the object. Representing the brightness of the illumination unit by B, the reflectivity of the object by R, the distance between the illumination unit and the object by l, and the optical transmitting coefficient of the transmission optical system, which conveys light from the illumination unit to the object, by k, the brightness L of the object is given by the following equation $$L = kBR/l^2 \quad (1)$$

In this equation, the values of the coefficient k and the brightness B are determined by the particular illumination unit used. The value of the reflectivity R remains substantially constant in a given environment of use. Specifically, for a medical endoscope, the value of the reflectivity R varies little over the internal wall of a coeliac cavity of a given internal organ and may be regarded as substantially constant, although it varies greatly when a different internal organ is observed. Hence, when observing or taking a picture of a given internal organ, it can be said that the brightness is inversely proportional to the square of the distance l as indicated by the equation (1) given above. With a lens such as is used in an endoscope in which a stop is located adjacent to the front focal point of an objective lens, the brightness of an image is proportional to the brightness of an object being observed, independently of the value of the magnification since the F-number is maintained constant. Accordingly, a measurement of the brightness of the image will provide an indication of the brightness L of the object given by the equation (1). As a result, a determination of the brightness of the object in this manner enables the distance to the object to be known through an arithmetic operation. The distance thus determined can be utilized in a focusing operation. The equation (1) can be rewritten into the following form:

$$l = (kBR/L)^{\frac{1}{2}} \quad (2)$$

Figure 1:
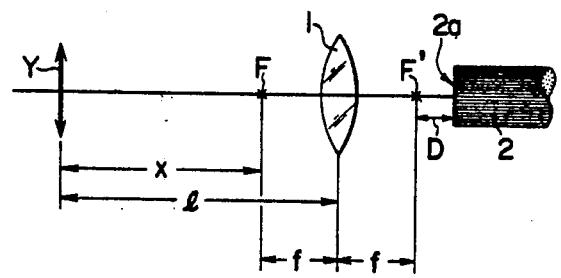
FIG. 1 is a schematic illustration of the principle of the focusing operation.

Referring to FIG. 1, a focusing operation which utilizes the distance l determined by the equation (2) will be described. FIG. 1 illustrates the focusing operation of a flexible endoscope, which includes an image guide 2 associated with an observation optical system and which is defined by a bundle of optical fibers. An objective lens 1 is disposed forwardly of the front end face 2a of the image guide 2. An object Y to be observed is spaced forwardly from the objective lens 1. Denoting the distance between the lens 1 and the object Y by l and the distance between the object Y and the front focal point F by x, it will be noted from FIG. 1 that an image of the object Y will be formed at a point which is spaced by a distance D from the rear focal point F'. From Newton's formula, the following equality applies:

$$xD = f^2 \quad (3)$$

The distance D signifies that a conjugate image plane 2a for the object Y is defined at the location of the front end of the image guide 2 which represents the light receiving surface of the endoscope. Since a focused image is transmitted to the image guide 2 formed by the bundle of optical fibers, the distance D is chosen to be a focusing travel in accordance with the invention. From the equation (3), it follows that:

$$D = f^2/x \quad (4)$$

where the distance x represents the distance l shown in FIG. 1 from which the focal length f is subtracted, so that the equation (4) can be rewritten as follows:

$$D = f^2/(l-f) \quad (5)$$

In general, the focal length f is much less than the distance l, and hence can be neglected, whereby the above expression can be written as follows:

$$D \approx f^2/l \quad (6)$$

Substitution of the equation (2) into the equation (6) results in:

$$D \approx f^2 \times \sqrt{\frac{L}{kBR}} \quad (7)$$

The equation (7) indicates that the focusing travel distance D can be derived by a determination of the brightness L of the object or light reflected from the object. In the arrangement of FIG. 1, the focusing travel distance D is achieved by moving the front end face 2a of the image guide 2 rearwardly through the distance D from the rear focal point F' of the objective lens 1. However, instead of moving the front end face 2a of the image guide 2, it should be understood that the focusing can be achieved by moving the objective lens 1 through the focusing travel distance D.

As mentioned previously, the value of the reflectivity R depends on the object to be observed. However, the value of the reflectivity R of several objects to be observed can be previously determined, and an average of such data may be used for practical purposes. For medical endoscopes, the value of the reflectivity R varies to a degree from patient to patient. However, the variation does not have so great a magnitude, so that where the same location or area is to be observed, the use of the above mentioned average value is sufficient for pratical purposes. As indicated by the equation (7), the influence of the reflectivity R upon the magnitude of the focusing travel D is proportional to the square root thereof, and hence it may be seen that the influence of varying values of the reflectivity R from individual to individual upon the accuracy of determination is relatively small.

Figure 2:
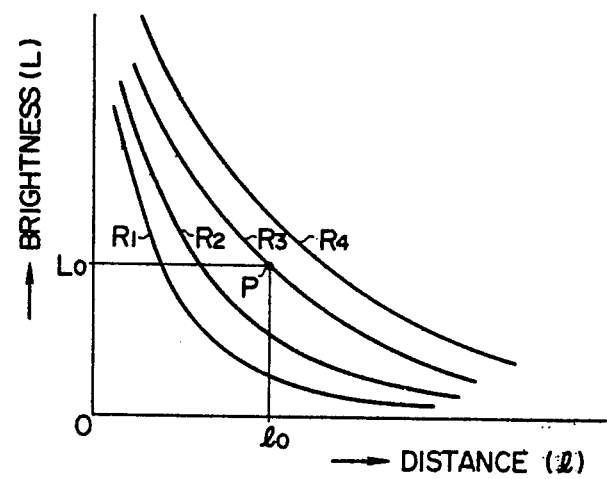
FIG. 2 graphically shows the relationship between the distance l to an object being observed and a corresponding brightness L for objects having different reflectivities $R_1$-$R_4$ and FIGS. 3 and 4 are schematic views illustrating the application of the invention to endoscopes of both the flexible type and the hard type.

The derivation of the distance l from the brightness L of the object will now be described. FIG. 2 illustrates the relationship defined by the equation (1) with the brightness L shown on the ordinate and the distance l on the abscissa. The light transmission coefficient k and brightness B depend on the particular illumination used. Consequently, curves representing the brightness L have varying gradients which depend on the values of the reflectivity R. Specifically, a number of curves can be obtained with the reflectivity R being chosen as a parameter ($R_1 - R_4$).

Assuming that a focusing operation is achieved manually to obtain the brightness $L_O$ and the distance $l_O$, the equation (1) is written as follows:

$$L_O = kBR/l_O^2 \quad (8)$$

The reflectivity R can be derived from the equation (8) in the following form:

$$R = L_O l_O^2 / kB \quad (9)$$

A point ($l_O, L_O$) defined by the brightness $L_O$ and the distance $l_O$ on the graph of FIG. 2 may be assumed to be point P. Then, a curve passing through this point is the controlling relationship between the brightness L and the distance l. Hence, a knowledge of brightness L permits the value of the distance l to be determined from this curve.

In the above description, the reflectivity R has been initially determined in order to derive the distance l from the brightness L. However, in practice, the value of the distance l can be determined without initially determining the reflectivity R. Thus, the substitution of the equation (9) into the equation (1) and a slight modification results in the following expression:

$$L = \frac{kB}{l^2} \cdot \frac{L_o l_o^2}{kB} \quad (10)$$

$$= L_o \left(\frac{l_o}{l}\right)^2$$

The distance l can be derived from the equation (10) in the following form:

$$l = l_o \sqrt{\frac{L_o}{L}} \quad (11)$$

The equation (11) indicates that the distance l to the object can be easily determined by a mere determination of the value of the brightness L of the object, provided the initial values of brightness $L_o$ and distance $l_o$ are known, without requiring any knowledge of the reflectivity R. The distance l determined can be used to derive the focusing travel D easily, in accordance with equation (5) or (6).

A focusing apparatus which operates based on the described principle of the invention, and representing one embodiment thereof, will now be described.

Figure 3:
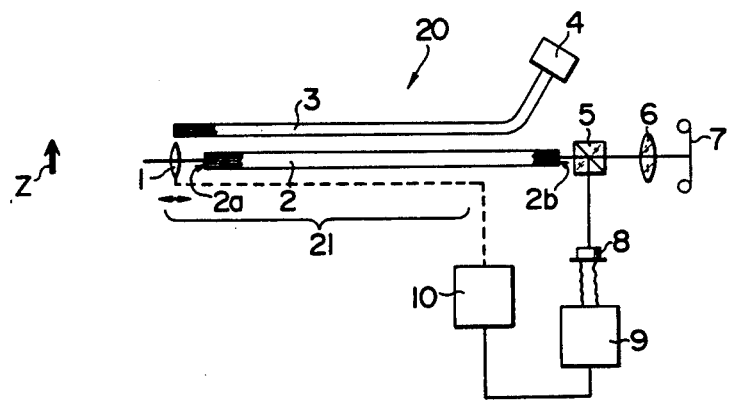

FIG. 3 shows a flexible endoscope 20 which includes an image guide 2 of an observation optical system which is formed by a bundle of optical fibers and, a light guide 3 for an illumination optical system which is also formed by a bundle of optical fibers and running in parallel relationship with the image guide 2. A light source 4 is disposed adjacent to the rear end of the light guide 3, and an objective lens 1 disposed forwardly spaced from the front end 2a of the image guide 2. A beam splitter 5 is disposed rearwardly spaced from the rear end face 2b of the image guide 2. A photoelectric transducer element 8 effects a photometry of part of light from the beam splitter 5. A signal processing circuit 9 responsive to an electrical output signal from the transducer element 8 and a servo mechanism 10 driven by an electrical output signal from the signal processing circuit 9 to control the position of the objective lens are also provided. An eyepiece and photographing lens 6 is disposed rearwardly spaced from the beam splitter 5 and allows an optical image delivered by the beam splitter to be viewed. It is to be understood that a photographic film 7 is disposed behind the photographing lens 6.

In the endoscope 20 described, numeral 21 represents a portion which includes the part of both the image guide 2 and the light guide 3 which is adapted to be inserted into a coeliac cavity or the interior of a machine. The light guide 3 and the light source 4 constitute together an illumination unit associated with the endoscope 20. Light from the source 4 passes through the light guide 3 to illuminate an object Z which is located forwardly of the objective lens 1. Light reflected from the object Z is transmitted through the objective lens 1 and passed through the image guide 2 to the beam splitter 5. Part of light from the beam splitter 5 is subject to photometry by the transducer element 8, which produces an electrical signal having a magnitude proportional to the amount of light incident thereon. The signal is applied to the processing circuit 9, which responds to the signal received to perform an arithmetic operation to develop a signal which drives the servo mechanism to achieve a focused position of the objective lens 1. It will be noted that the arithmetic operation which takes place within the signal processing circuit 9 is that of deriving the distance l from the electrical output signal in accordance with the equation (11) and deriving the focusing travel D in accordance with the equation (5) or (6). These arithmetic operations can be easily performed by utilizing a well known microcomputer or wired logic. It is to be understood that the initial values of brightness and distance $L_o$ and $l_o$ are previously determined and stored before the arithmetic operation takes place.

When the processing circuit 9 derives the focusing travel D, it drives the servo mechanism 10 through an output circuit, not shown, in accordance with the value of the focusing travel D, thus moving the objective lens 1 through the travel D. In this manner, the objective lens 1 can be focused on the object Z.

On the other hand, an optical image from the beam splitter 5 is transmitted through the eyepiece and photographing lens 6 to impinge on the film 4 through a shutter, not shown. After the combination of the processing circuit 9 and the servo mechanism 10 has established a focused position of the objective lens 1, the shutter is activated to permit a picture to be taken.

The above description is directed to the application of the invention to the flexible endoscope 20 which utilizes bundles of optical fibers. The invention can be quite similarly applied to an endoscope of the hard type which utilizes relay lenses in place of optical fibers. Such an arrangement will be described with reference to FIG. 4.

Figure 4:
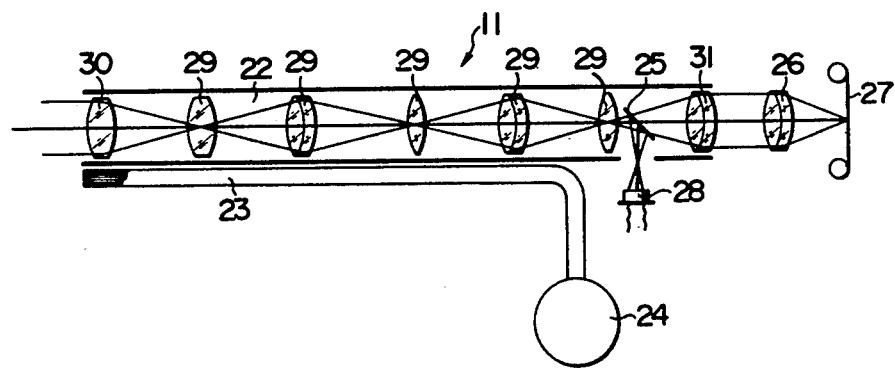

FIG. 4 schematically shows the essential part of an endoscope 11 of the hard type to which the invention is applied. An observation optical system 22 comprises a relay lens assembly including a plurality of lenses 29 and an objective lens 30. Beam splitter 25, eyepiece 31, photographing lens 26 and film 27 are disposed rearwardly of the lenses 29 generally in the same manner as shown in FIG. 3. A photoelectric transducer element 28 is disposed below the beam splitter 25 for effecting photometry of the part of the light from the relay lenses 29 which is diverted by the beam splitter 25. A light guide 23 formed by a bundle of optical fibers to define an illumination optical system is located adjacent to the observation optical system 22, and a light source 24 which constitutes an illumination system together with the light guide is disposed adjacent to the rear end of the light guide 23.

The endoscope shown in FIG. 4 operates in the same manner in principle as the endoscope 20 shown in FIG. 3, illuminating an object to be observed by supplying light from the source 24 through the image guide 23, transmitting the reflected light through the objective lens and the relay lens assembly 29 to the beam splitter 25, and effecting photometry by means of the transducer element 28. The transducer element 28 produces an output signal, which is not shown, but which is applied to a known signal processing circuit like that shown at 9 in FIG. 3. An output of the processing circuit is applied to a conventional servo mechanism like the servo mechanism 10 shown in FIG. 3, thus effecting a focusing operation of the endoscope 11.

It is to be noted, however, that with the endoscope of the hard type, the output of the servo mechanism is utilized to move the photographing lens 26 which effects a focusing operation. However, it should be understood that a focusing operation can be achieved by a movement of either objective lens 30, relay lens assembly 29 or eyepiece 31. In the endoscope of the hard type, a light receiving surface of the observation optical system is located on the film surface, so that the focusing takes place so that a conjugate image plane of the object coincides with the film surface.

The above covers a description of an automatic focusing operation. Instead of providing an automatic focusing, a photometric value or a focusing travel may be displayed, and a focusing operation may be manually effected in accordance with the displayed value. In this instance, part of the signal processing circuit and the servo mechanism can be dispensed with.

It is to be noted that the location of the transducer element is not limited to the one shown in the drawings, but the transducer element may be located anywhere on the front end of an intermediate position of the endoscope or adjacent to the eyepiece. In addition, the transducer element may be provided in the form of an attachment which is separate from the endoscope.

What is claimed is:

1. A method for focusing an observation optical system which is receiving light reflected off an object being illuminated by an illumination optical system associated with said observation optical system, said observation optical system having at least two elements whose relative position determines the focus of said observation optical system with respect to said object, said method comprising the steps of:
   (a) measuring the brightness of said object while the relative positions of said at least two elements are fixed with respect to one another;
   (b) arithmetically determining the location of said object as a function of said measurement; and
   (c) adjusting the relative positions of said at least two elements as a function of said determination so as to bring said object into focus by said observation optical system.

2. A focusing method according to claim 1, wherein said adjusting step comprises the step of moving at least one of said elements to a location which will cause an image receiving plane of said observation optical system to coincide with a conjugate image plane of said object.

3. A focusing method according to claim 2, wherein said at least two elements comprise an objective lens and a fiber optics bundle and wherein said moving step comprises the step of moving said objective lens.

4. A focusing method according to claim 2, wherein at least two elements comprise an objective lens and a fiber optics bundle and wherein said moving step comprises the step of moving said fiber optics bundle.

5. A focusing method according to claim 2, wherein said at least two elements comprise an objective lens and an eyepiece and wherein said moving step comprises the step of moving said objective lens.

6. A focusing method according to any one of claims 3-5, wherein said determining step comprises the step of arithmetically determining the distance of said object from said objective lens.

7. A focusing method according to claim 1, wherein said determining step comprises the step of arithmetically determining the distance of said object from said observation optical system.

8. A focusing method according to claim 1, wherein said adjusting step comprises the steps of:
   arithmetically determining how far the position of one of said elements must be moved to bring said object into focus; and
   moving said one element by said determined amount.

9. Apparatus for focusing an observation optical system which is receiving light reflected off an object being illuminated by an illumination optical system associated with said observation optical system, said observation optical system having at least two elements whose relative position determine the focus of said observation optical system with respect to said object, said apparatus comprising:
   (A) first means for measuring the brightness of said object while the relative positions of said at least two elements are fixed with respect to one another; and
   (B) second means for both determining the location of said object as a function of said measurement and adjusting the relative position of said at least two elements as a function of said determination so as to bring said object into focus by said observation optical system.

10. Apparatus according to claim 9, wherein said second means moves at least one of said elements to a location which will cause an image receiving plane of said observation optical system to coincide with a conjugate image plane of said object.

11. Apparatus according to claim 10, wherein said at least two elements comprise an objective lens and a fiber optics bundle and wherein said second means moves said objective lens to bring said object into focus.

12. Apparatus according to claim 10, wherein said at least two elements comprise an objective lens and a fiber optics bundle and wherein said second means moves said fiber optics bundle to bring said object into focus.

13. Apparatus according to claim 10, wherein said at least two elements comprise an objective lens and an eyepiece and wherein said second means moves said objective lens in order to bring said object into focus.

14. Apparatus according to any one of claims 11-13, wherein said second means determines the location of said object by arithmetically determining the distance of said object from said objective lens.

15. Apparatus according to claim 9, wherein said second means determines the location of said object by arithmetically determining the distance of said object from said observation optical system.

16. Apparatus according to claim 9, wherein said second means comprises:
   means for arithmetically determining how far the position of one of said elements must be moved to bring said object into focus; and
   means for moving said one element by said determined amount.

17. Apparatus according to claim 9, wherein said second means comprises:
   (A) means for determining the location of said object as a function of said measurement; and
   (B) means for adjusting the relative positions of said at least two elements as a function of the location of said object so as to bring said object into focus.

* * * * *